(12) United States Patent
Srinivasan

(10) Patent No.: US 8,475,639 B2
(45) Date of Patent: Jul. 2, 2013

(54) TITRATION DEVICE AND METHOD

(75) Inventor: Kannan Srinivasan, Tracy, CA (US)

(73) Assignee: Dionex Corporation, Sunnyvale, CA (US)

( * ) Notice: Subject to any disclaimer, the term of this patent is extended or adjusted under 35 U.S.C. 154(b) by 651 days.

(21) Appl. No.: 11/952,013

(22) Filed: Dec. 6, 2007

(65) Prior Publication Data

US 2009/0145777 A1 Jun. 11, 2009

(51) Int. Cl.
*C25B 1/46* (2006.01)

(52) U.S. Cl.
USPC .................................. 204/405; 205/778.5

(58) Field of Classification Search
USPC ............... 205/405, 788.5; 422/100; 204/405
See application file for complete search history.

(56) References Cited

U.S. PATENT DOCUMENTS

| 2,744,061 | A |   | 5/1956  | Ford et al.  |         |
|-----------|---|---|---------|--------------|---------|
| 2,954,336 | A |   | 9/1960  | Grutsch      |         |
| 3,032,493 | A |   | 5/1962  | Coulson et al. |       |
| 3,308,041 | A |   | 3/1967  | Strickler    |         |
| 3,374,161 | A | * | 3/1968  | Zatz         | 204/405 |
| 3,856,633 | A |   | 12/1974 | Fletcher, III |        |
| 4,007,105 | A |   | 2/1977  | Buzza et al. |         |
| 4,152,215 | A |   | 5/1979  | Yoshino et al. |       |
| 5,045,204 | A |   | 9/1991  | Dasgupta et al. |      |
| 6,129,832 | A | * | 10/2000 | Fuhr et al.  | 205/775 |
| 6,225,129 | B1|   | 5/2001  | Liu et al.   |         |
| 2002/0182741 | A1 | * | 12/2002 | Liu et al. | 436/161 |

FOREIGN PATENT DOCUMENTS

| EP | 1685887 A1 | 8/2006 |
| EP | 1867384 A1 | 12/2007 |
| WO | WO 97 18503 A1 | 5/1997 |
| WO | WO 99 38595 A1 | 8/1999 |

OTHER PUBLICATIONS

Dean, J.A. Gravimetric and volumetric analysis. Analytical Chemistry Handbook, Chapter 3, McGraw Hill (1995).

* cited by examiner

*Primary Examiner* — J. Christopher Ball
(74) *Attorney, Agent, or Firm* — David J. Brezner

(57) ABSTRACT

A titration apparatus comprising a titration reservoir for a non-flowing sample solution to be titrated; an ion source reservoir comprising an ion source solution of selected ions; an ion exchange membrane barrier capable of passing ions from the ion source solution to the titration reservoir, but of blocking bulk liquid flow; a first electrode in electrical communication with the ion source reservoir; and a second electrode in electrical communication with the titration reservoir. Also, an electrolytic titrant generator for use in the titration apparatus.

13 Claims, 4 Drawing Sheets

TITRATION DEVICE AND METHOD

BACKGROUND OF THE INVENTION

The present invention relates to a titration device and method and, more particularly to one using electrolytic titrant generation.

Determining the total acidity or alkalinity of a sample is now a routine part of characterizing a sample in many industrial laboratories. A simple way to pursue this measurement uses a volumetric titration apparatus including a volumetric burette from which the appropriate titrant, usually acid or base titrant, is added to a stirred sample while monitoring sample characteristics such as pH or conductivity. From the characteristic plot of detector response versus volume of the titrant and the associated endpoint, the equivalents of acid or base in a given sample is determined. The field of titration is over 100 years old, and there is significant literature covering various aspects of titration. There are also several books in basic analytical chemistry that cover the basic aspects of titration theory and the determination of the end point (For example Chapter 3 entitled Gravimetric and Volumetric Analysis, Analytical Chemistry HandBook, by John A. Dean, McGraw Hill Inc, 1995).

Modern titrators use an automated means of dispensing the liquid titrant, for example, by using a motorized syringe. The dispensing of the titrant is done in a constant mode with each increment having a constant volume or in a dynamic mode where the titrant is added in large aliquots and near the end point the addition frequency is reduced to get an accurate determination of the end point. The dynamic mode expedites the analysis and reduces the analysis time. Despite the advances, modern titrators still use liquid titrant reagents that need to be frequently prepared and replenished to ensure no degradation or build up of contaminations. For example titration with a base titrant results in a carbonate error with an indicator with a basic transition point (phenolphthalein). For basic titrants proper precautions during preparation and storage needs to be taken.

Coulometry is an established methodology in the field of titration. Typically, in volumetric titration the volume of liquid titrant required to neutralize the acid or base in a sample is measured. In a coulometric titration the titrant is generated electrochemically and the quantity of electric charge is measured. Coulometry titration could be classified as primary and secondary titration. In the primary titration methods the titrant is directly derived from the electrode. Examples of this type of electrodes are silver metal, mercury, or mercury amalgam or electrodes coated with silver-silver halide and they generate the ions required for the titration for example silver metal anode forming silver ions that can be used to titrate chloride. Secondary titration methods are much more popular and use an intermediate ion generated from a precursor that is added to the supporting electrolyte. The intermediate ions must be generated with 100% current efficiency and must react rapidly and stoichiometrically with the substance being determined. For example during the coulometric titration of Fe (II) to Fe (III), the method will not be 100% current efficient unless excess Ce (III) is added as the precursor to the supporting electrolyte sulfuric acid.

The current in a coulometric titration is usually maintained constant and by monitoring the time in seconds, the number of coulombs required to titrate a species and hence the number of equivalents is easily derived. Detection of the end point of the titration occurs via conventional means such as color change from addition of an indicator. Other means such as using an amperometric, pH or conductivity detection is also routinely used.

A review of literature indicates there are several patents and publications relating to various aspects of titration. U.S. Pat. No. 2,744,061 discloses a titration apparatus in which the reagent is prepared in a separate cell from the titration cell and the reagent is then introduced into the titration vessel. Such a scheme produces acid and base from electrolysis of 1 M sodium sulfate solution and one or the other stream could be introduced for titration. The method suffers from a) sample dilution errors b) need to control the flow of the sodium sulfate feed c) addition of salt solution to the sample since not all of the electrolyte was used for the formation of acid or base and this would limit the detection to detectors that are sensitive to the presence of salt. For example conductivity detectors cannot be used in the above scheme because the conductivity of the 1 M salt solution will overwhelm the detector response making it difficult to detect small changes in conductivity from the presence of small amounts of acid or base.

Another version of a coulometric titration apparatus using the silver ions generated from a silver anode is discussed in U.S. Pat. No. 3,032,493. Yet another version of a titration device is discussed in U.S. Pat. No. 3,308,041. This is a continuous titration device for process applications. The titrant is generated coulometically and then mixed with the liquid sample to form reactant product which is directed to the sensing means for detection. Also some feedback mechanism between the sensing and the titrant is discussed that allows control of the generated titrant.

U.S. Pat. No. 3,856,633 discloses a concentration measurement technique that uses coulometrically generated silver ions from a silver anode and a platinum cathode in the presence of sample cyanide ions. Silver ions react with the cyanide ions lowering the free silver ion availability which is then monitored across a silver sulfide membrane by a potential measurement. The free silver ions unreacted with the sample are on one side of the membrane, and a standard with a known quantity of silver ions is on the other side of the membrane. From the developed potential a detection scheme was available for the sample ions. In another embodiment the silver sulfide membrane was placed between the silver anode and the platinum cathode to protect the silver anode from exposure to reactive species such as nitrate in the sample.

U.S. Pat. No. 4,007,105 discloses a titration apparatus for coulometric titration of chloride in blood samples that uses a silver anode and a platinum cathode in an acid electrolyte medium. The silver ions generated in proportional to an applied current reacts with the chloride in the sample forming silver chloride and the titration is monitored using a pair of amperometric electrodes. Also disclosed is the arrangement of the electrode cells.

In many of the above approaches since the oxidation or reduction of the analyte ions occur at the generation electrodes, as the solution is depleted of analyte an effect called concentration polarization occurs. The potential must therefore increase to maintain the constant current operation. This higher potential in turn results in lower current efficiency due to undesired side reactions on the electrode surface.

While conventional coulometric titration require all of the analyte to be reacted, a version of this approach called "flash titration" where only a portion of the sample stream in the vicinity of the electrode is titrated significantly reduced the overall titration time. Since the methodology is a diffusion regulated process, the method is sensitive to varying diffusion rates of various sample acids and bases, temperature and sample viscosity. A calibration step called the matrix adjustment factor is needed to compensate for the above effects.

SUMMARY OF THE INVENTION

One embodiment of the invention is a titration apparatus comprising a titration reservoir for a non-flowing sample solution to be titrated; an ion source reservoir comprising an ion source solution of selected ions, positive or negative; an ion exchange membrane barrier capable of passing ions of one charge, positive or negative, from said ion source solution to said titration reservoir, but of blocking bulk liquid flow; a first electrode in electrical communication with said ion source reservoir; and a second electrode in electrical communication with said ion source reservoir, said first electrode being inert when a current is applied between said first and second electrodes.

Another embodiment is an electrolytic titrant generator for use in a titration apparatus, comprising an ion source reservoir; a first electrode disposed in said ion source reservoir; an ion exchange membrane barrier having first and second sides, the first side being adjacent to said ion source reservoir and capable of transporting ions of one charge, positive or negative, but of blocking bulk liquid flow, and a second electrode disposed adjacent to the second side of the membrane barrier, said titrant generator not including a titration reservoir for sample solution to be titrated but being configured to be immersed in sample solution in a titration reservoir.

An additional embodiment is an electrolytic method for titrating a liquid sample using a titration apparatus of the foregoing type. The method comprises applying an electrical potential between the first and second electrodes to cause the selected ions to be transported from an ion source reservoir through the membrane barrier into sample solution in the titration reservoir to titrate the sample solution to an end point, the first electrode being inert during application of the potential, and detecting the titration end point.

DETAILED DESCRIPTION OF PREFERRED EMBODIMENTS

The invention includes the embodiments of an electrolytic titrant generator, a titration device which incorporates an electrolytic titrant generator, and a method of titrating using such a device. The invention will first be described with respect to the titrant generator.

The titrant generator may be in the form of a portable device which can be mounted to a titration reservoir which typically includes a non-flowing sample solution to be titrated. In general, the titrant generator operates as follows. Ions are transported into the titration reservoir of sample solution from an ion source solution in a separate chamber of the generator through an ion exchange membrane barrier. A first electrode is disposed in the ion source reservoir and a second electrode is disposed adjacent to the other side of the membrane barrier from the ion source reservoir. For portability, the titrant generator may be separate from the titration reservoir but is configured to be immersed in the sample solution. Thus, it is small enough to be immersed in the sample solution of a titration reservoir. The principles for supplying the ions for titration from an aqueous ion source reservoir or transport across a membrane barrier into an aqueous solution on the other side of the barrier under the influence of an electric field are analogous to the operation of an electrolytic eluent generator such as disclosed in U.S. Pat. No. 6,225,129. Such principles and the different devices disclosed in the '129 patent are incorporated herein by reference.

Figure 1:
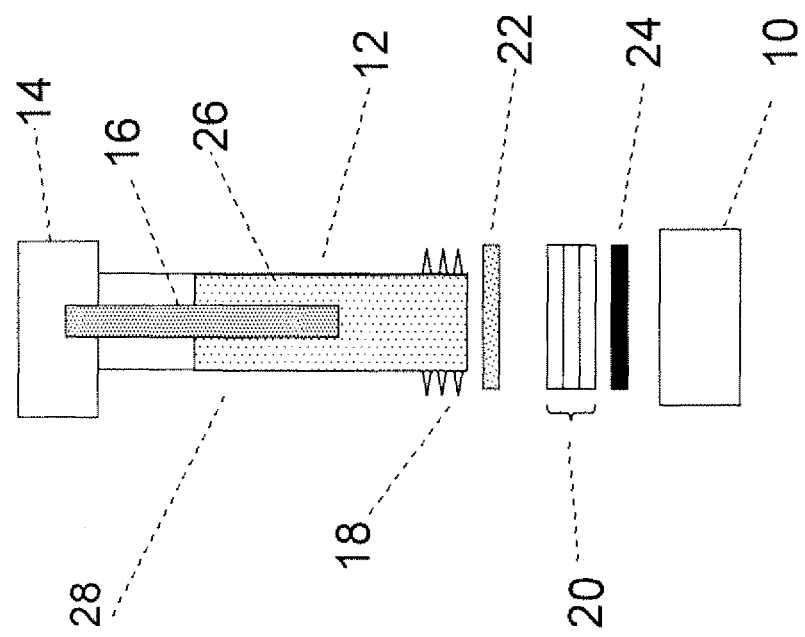
FIG. 1 is an exploded schematic view of a titrant generator according to the invention.

One form of titrant generator is assembly 28 illustrated in the exploded schematic view of FIG. 1. It includes an ion source reservoir or container 12 which is filled with a source of selective positive or negative ions 26. Such source may be an aqueous solution of an acid, base, or salt or may be ion exchange resin with exchangeable ions of the selected ions. An electrode 16 is mounted to project into the ion source in container 10 in electrical contact therewith. As illustrated, electrode 16 is mounted to an optional container cover 14 which encloses container 12 and routes the electrical connections for electrode 16. A gas vent may be included for container 12, such as in cover 14, to remove electrically generated gases from the container. A membrane barrier 20, which may comprise one, two, three, or more ion exchange membranes, is mounted across container 12 in sealing engagement therewith near the container bottom. As illustrated, assembly 28 is in cylindrical form. Thus, the ion exchange membranes of barrier 20, three in number as illustrated, are in a stacked disc configuration.

Membrane barrier 20 substantially blocks flow of liquid. As used herein, substantially blocking means blocking all flow except a small amount of liquid leakage. Preferably, essentially all bulk liquid flow is blocked. The barrier could be a single ion exchange membrane or one or more ion exchange membranes could be used as the barrier. Preferably the number of membranes in the barrier is less than 10, more preferably less than 7 and most preferably less than about 4, specifically 1-3 membranes. The rationale for having multiple membranes is to minimize leakage of the ion source solution into the sample and to substantially block sample flow back into the ion source solution.

Electrode 24 is disposed near the bottom of generator 28 for contact with sample solution in a titration reservoir adjacent to membrane barrier 20 on the opposite side of the membrane from container 12. An enclosure 10 with an opening 10A (not shown) is used to hold electrode 24 and ion exchange membrane barrier 20. Enclosure 10 is sealed to container 12 using an "O" ring seal 22 which may be formed of an inert plastic material, such as Teflon, using an appropriate mounting mechanism such as male machine threads 18. In the illustrated embodiment, enclosure 10 has internal (female) threads which mate with male threads 18 on the bottom of container 12 to enclose seal 22, membrane barrier 20, and electrode 24 to make a leak-free seal. Opening 10A, termed an output cavity, is fitted with electrode 24 for exposure to the sample solution in a titration reservoir.

Figure 2:
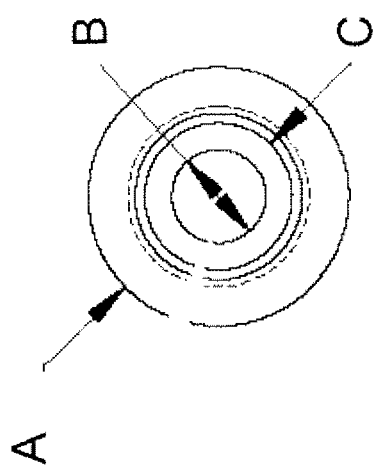
FIG. 2 is a top view of the enclosure of the titrant generator or FIG. 1.

FIG. 2 shows a top view of enclosure 10. The outer diameter of the enclosure is designated A; the internal opening of the output cavity 10A fitted with the electrode and the membranes is designated "B"; and the sealing surface on which the "O" ring seal is mounted to seal with a lower portion of the ion source reservoir container 12 is designated "C".

Container 12 of assembly 28 is filled with the ion source solution through an inlet in lid 14 or by removing the lid. Electrode 24 at the bottom of the assembly is in open contact with a sample solution in a titration reservoir when immersed therein as part of a complete titration apparatus. Generator assembly 28 may be mounted, directly or indirectly to a titration reservoir, preferably in an orientation so that the exposed surface of electrode 24 is immersed in the titration solution. In a preferred embodiment, electrode 24 is substantially planar with one of its planar surfaces proximal to membrane barrier 20 and its surface distal to the membrane barrier exposed for direct contact with the titration solution. Suitably, a large portion of this distal surface of electrode 24 is exposed to the environment so that when it is immersed in a titration reservoir of solution to be titrated, a large surface area of electrode 24 is available for the transmission of electrodes through the membrane and electrode. In an alternative embodiment, not shown, a removable cover may be placed over the electrode to protect it for shipment or the like which is removed prior to use during titration.

In other embodiments, not shown, the titrant generator may be in a form other than a cylinder, such as one having a rectangular cross-section. Similarly, electrode 24 need not be of the same cross-section and orientation as membrane barrier 20 so long as it is an electrical communication with the membrane when immersed in the titrant solution. As illustrated, membrane barrier 20 contacts electrode 24. However, there may be space between them. Also, membrane barrier 20 may be in direct contact with the titrant solution.

The electrodes and the membranes in any shape or configuration preferably closely match the output cavity in the titration device. It is desirable that the output cavity have a small delay volume thereby eliminating any issues with sweep out from the cavity. If the delay volume is too large then it may be difficult to remove the generated titrant and disperse it into the sample. Preferably the output cavity is of the same dimension as the exposed electrode area to the sample. The electrode surface area expressed as a percentage of the open output cavity is preferably in the range of 5-100%, more preferably at least 50% or 80% and most preferably about 100%.

In a preferred embodiment, electrodes 16 and 24 are inert to acid or base when a potential is applied across them. As used herein, the term "inert" excludes the materials that would be substantially degraded under the electrolytic conditions of titration and electrodes which would serve as the source of the selected titration ions. Thus, the preferred inert electrodes exclude silver electrodes used as a source of silver ions in the prior art. Preferred inert materials for electrodes include noble metals such as platinum, palladium, iridium and the like.

Figure 3:
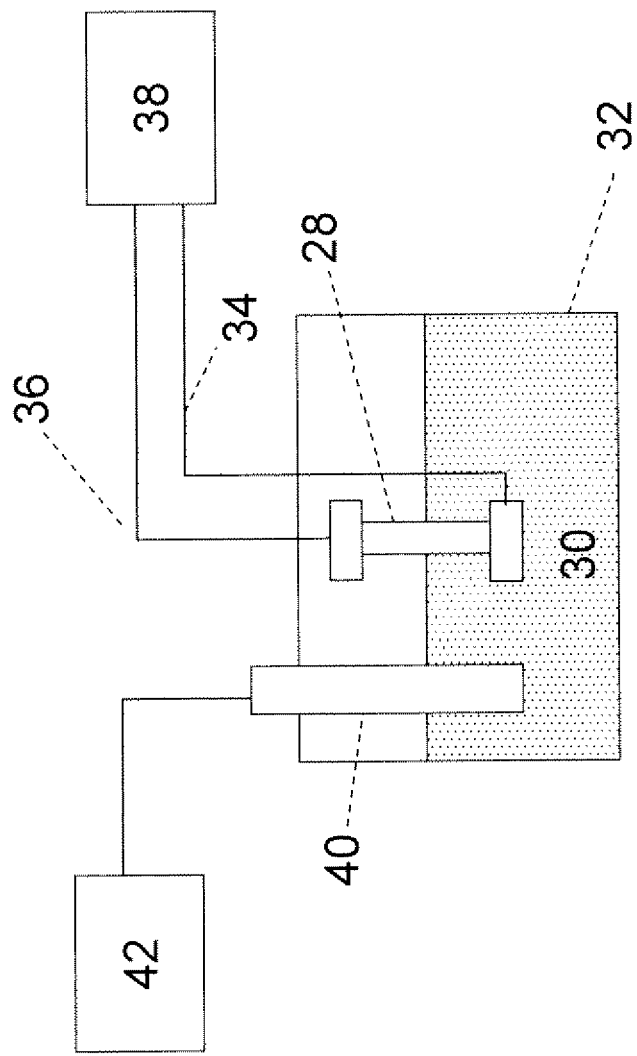
FIG. 3 is a schematic view of a titration system according to the invention.

FIG. 3 illustrates a titration device according to the present invention which includes a titrant generator assembly 28 as described in FIG. 1. In the illustrated titration device, the titrant generator component may be in the form of the described portable generator which is suitably mounted to the titration tank by a clamp or the like. Alternatively, the titrant generator may be a non-portable component constructed and directly mounted to project into the tank.

Referring specifically to FIG. 3, titration reservoir 32 is illustrated including an aqueous sample solution 30 to be titrated. In a preferred embodiment, solution 30 is substantially non-flowing during titration. A stir bar with a stirrer (not shown) may be used for mixing the sample so that the titrant is mixed efficiently with the sample to neutralize the sample. As used herein, stirred solution is considered non-flowing.

As illustrated, the titrant generator 28 is of the type illustrated in FIG. 1. It is powered using a DC power supply 38 connected by electrical lines 34 and 36. A detector probe 40, e.g. a pH or conductivity probe, is installed to project into the solution in reservoir 32 to monitor the progress of the titration. Detector probe 40 is connected to an appropriate detector 42 such as a pH or conductivity detector.

In operation for generation of base titrant for use in titrating an acid sample, container 12 is filled with a cation source that would supply the cations required for the base formation. For example, for preparing sodium hydroxide titrant, the source could be a source of sodium, such as an aqueous solution sodium hydroxide concentrate. The electrodes 16 and 24, not sources of the titrant ions, are made from inert metal platinum foil. Electrode 16 is designated in this embodiment as the anode. The enclosure 10 is fitted with a platinum foil 24 which is designated as a cathode, followed by three layers of cation exchange membrane 20. The Teflon "O" ring 22 is installed next and the enclosure 10 is fitted on to the conduit 12. With titrant generator assembly 28 assembled, electrode 24 is exposed at the bottom of the assembly. Electrode 24 is available for water splitting reactions and for titrant generation and resides in near proximity to ion exchange membrane barrier 20 in cation form, i.e. including exchangeable cations. For generating anions for an acid titrant, all polarities are reversed, the titrant generator assembly 28 is assembled with anion exchange membrane, and the container 12 is filled with an anion source that would supply the anions required for the acid formation.

Electrode 24 is in contact with the sample solution 30. Upon applying a potential large enough to split water, hydronium ions are generated at the anode 16 while hydroxide ions are generated at the cathode 24 by the water splitting reactions at the electrode surfaces.

The titrant concentration generated with 100% faradic efficiency can be calculated from the equation:

$$C=60I/F \qquad \text{(Equation 1)}$$

I is the current in amperes
F is Faraday's constant (96500 coulombs/equiv)
C is the concentration of titrant generated at any instance and is expressed as M or eqv A current of 50 mA will generate 31.088 μeqv of titrant.

Based on the time t in minutes required to neutralize the acid or base sample the gram mill equivalents of the acid or base in the sample can be calculated as $$m.eq = I \times 60 \times t/F \qquad \text{(Equation 2)}$$

It should be noted as per the present invention the water required for the water splitting reaction at the cathode is derived from the sample solution. The sodium ions are driven from the container 12 through the cation exchange membrane barrier 20 and combine with the hydroxide generated at the cathode to form sodium hydroxide titrant. The sodium hydroxide titrant is now dispersed in the sample for neutralization of acids in the sample. No substantial change in the sample volume is observed. For each hydroxide generated at the cathode one sodium ion is transported into the sample solution. For each hydroxide generated at the cathode, the hydronium ion generated at the anode is consumed in neutralizing the base in the source container. Over time, the base in the source container is depleted and is converted to a more dilute form. By monitoring the voltage across the container, the source ions could be replenished.

The volume of the ion source container 12 is suitably from about 1 ml to 2000 ml; more preferably from 5 ml to 1000 ml and most preferably from about 10 ml to about 400 ml. The concentration of the source when using a liquid source would preferably be less than 10 M, more preferably less than about 4 M, and most preferably less than about 2 M. The applied current for titrant generation is preferably less than about 2 A more preferably less than about 400 mA and most preferably less than about 100 mA. The ion source container could be replenished when needed in an automated manner using known methods.

Advantages of the titrant generation system of the present invention include:

(1) There is minimal change in the sample volume and hence any error associated with sample dilution is substantially eliminated by the present invention;

(2) Since the titrant is consumed immediately in the neutralization reactions there is no issue with intrusion of dissolved gases such as carbon dioxide and associated carbonate error;

(3) The titrant is prepared in the purified form as and when needed in proportion to the applied current there are no issues with storage (both short term and long term storage) or contamination;

(4) The titrant generation occurs in an automated fashion eliminating errors from preparation; and (5) There are no issues with concentration polarization and associated need to increase the potential. The titrant generation is decoupled from analyte interaction as per the present invention.

The present invention overcomes limitations of coulometric titrations such as (a) a need for electrode derived reagents since the current method uses inert noble metals for purely water splitting reactions; (b) a need to add precursor for generation of intermediate ions; and (c) a need to pursue matrix factor adjustment as mandated by flash titration method.

The base titrant generator of the present invention when combined with the acid generator of the present invention could generate both acid and base titrants on demand. The titrant devices thus could allow back titration applications. In the simplest form in this embodiment the titrator generators are two separate devices. It is also possible to integrate the two devices to have one source container such as a salt and form the acid or base from the anion or cation of the source form of the salt. In one embodiment the device would be a "H" shaped device with the two vertical components comprising of two titrant assemblies 28 which have anion exchange membranes for acid generation and cation exchange membranes for base generation respectively with appropriate polarity of the electrodes as discussed previously. The horizontal "H" portion would be a conduit connecting the acid and base assemblies 28 so there is fluidic communication between the two vertical sections. In operation the electrodes 24 and 16 of the respective assemblies would be powered to create acid or base titrant in response to the applied current, as the case may be.

EXAMPLE 1

Base titrant generator: A 9×100 mm chromatographic column PEEK hardware from Dionex Corporation was used in this example. The end fitting detail is shown in FIG. 2. These modifications allowed electrode and membrane stack to be assembled as shown in FIG. 1. A Teflon "O" Ring was used to make the final seal against the 9×100 mm conduit or container. The electrode was made from a perforated platinum foil of 0.001" thickness and was cut in the shape of a circle with a diameter of 0.5". The cation exchange membrane CMI 7000 was obtained from Membrane International, Inc. (Glen Rock, N.J.) and cut in the shape of a circle with a diameter of 0.5". Three pieces of the membrane was used in the above assembly. An anode was a rectangular piece of a platinum electrode (1×6") that was placed in the 9×50 mm column as shown in FIG. 1. The electrodes were connected using platinum wire and then connected using normal leads with alligator clips to a DC power supply (HP). A 2 M NaOH solution was prepared from a stock solution of 50% NaOH (Sigma Aldrich, St. Louis, Mo.) and was used as the source concentrate in the 9×100 mm column.

EXAMPLE 2

Figure 4:
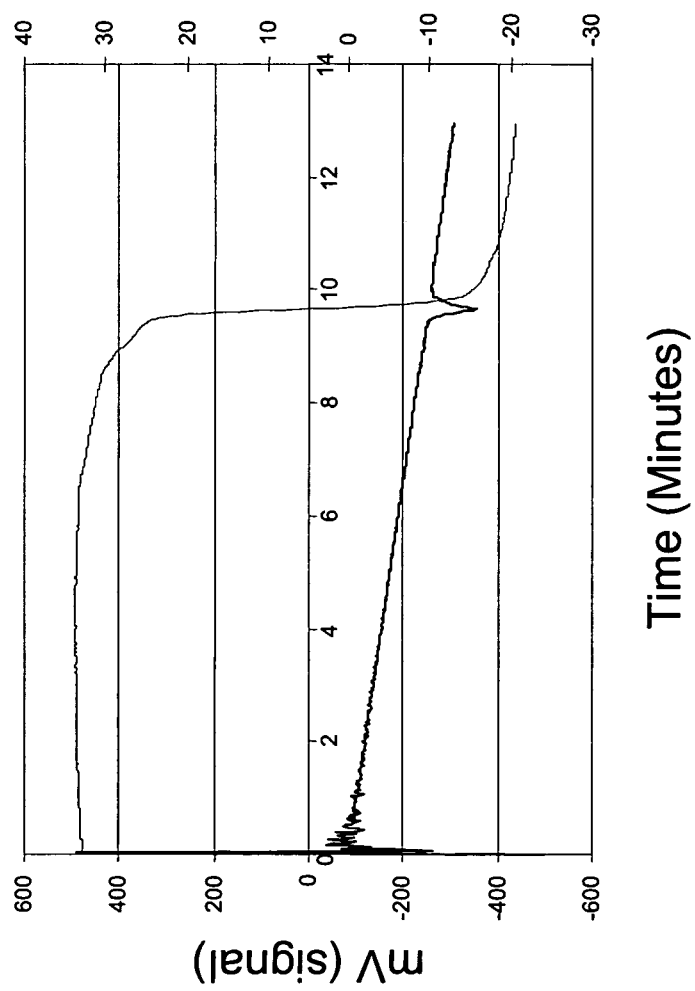
FIG. 4 is a graph plotting experimental titration results using the method of the invention.

The titrant generator from Example 1 was placed in a sample container (50 ml beaker) and was oriented in the vertical direction roughly above 2" from the bottom of the container using a clamp. A pH probe (A EG50 Combination pH/Ag—AgCl electrode from Dionex Corporation, Sunnyvale, Calif.) was used as the probe to monitor the progress of the titration. The output from the pH meter was plotted as mV signal. A sample containing 20 mM Methane sulfonic acid was prepared accurately from a stock concentrate of Methane sulfonic acid (Sigma Aldrich Chemicals, St. Louis. MO) and 15 ml of the prepared acid was added to the sample container. The titrant generator was powered at 50 mA constant current conditions. The setup was similar to what is shown in FIG. 2. A stir bar was placed in the container and the solution was stirred using a stirring plate. The progress of the titration was monitored. Since the sample was accurately known (20 mM×15 mL=300 ueqv) it was possible to calculate the expected equivalence point based on an applied current of 50 mA or generation of 31.056 µeqv of base per minute. The theoretical equivalence point is calculated as 9.660 minutes. A plot of the monitored potential versus time and the derivative plot showed the equivalence point to be very close to the theoretical number and were estimated to be 9.667 minutes as shown in FIG. 4. This shows excellent correlation between the theory and practical observation. This also validates the utility of the titrant generator as per the present invention.

EXAMPLE 3

The device of Example 1 was tested at 200 mA generating a high concentration of titrant. (124 µeqv/min). The device was able to titrate successfully 600 µeqv of acid as shown in Table 1.

TABLE 1

| Sample | Sample Conc mM | Sample Volume mL | Current mA | Expected Time (Min) | Observed Time (Min) |
|---|---|---|---|---|---|
| HCl | 60 | 10 | 200 | 4.83 | 4.81 |
| HCl | 10 | 10 | 40 | 4.03 | 4.07 |
| MSA | 10 | 10 | 40 | 4.03 | 4.09 |

The device voltage was monitored and when the device voltage increased by 10 V the source concentrate was replenished. The device was also tested with other samples and conditions as listed in Table 1. The setup was semi automated in that the start time was triggered manually. Good correlation between theory and experiment was realized.

EXAMPLE 4

Acid titrant generator: The hardware from example 1 was used for assembling the acid generator as per the present invention. All aspects of the assembly were similar to example 1 except anion exchange membranes AMI 7001 from Membrane International, Inc. (Glen Rock, N.J.) were used in place of the cation exchange membranes. A 2 M Methane sulfonic acid solution was prepared from the concentrated acid obtained from Sigma Aldrich, St. Louis, Mo. and was used as the source concentrate in the 9×100 mm column. The polarity of the electrodes was reversed with the electrode in contact with the sample being the anode and the electrode in contact with the acid source being a cathode. The device is now suitable for acid generation.

EXAMPLE 5

A sample comprising of 20 mM NaOH×5 mL or 100 μeqv was added to a sample container as before and was tested with the acid generator of example 4. Approximately 20 mL of DI water was added to ensure that the acid generator and the pH probe were fully immersed in the sample container. The setup was tested at a current of 50 mA which corresponded to roughly 31 μeqv of acid and was used to neutralize the base. The expected time for completion of neutralization was 3.22 minutes and the observed time was 3.24 minutes suggesting excellent correlation with theory.

What is claimed is:

1. A titration apparatus comprising:
    (a) a titration reservoir for a non-flowing sample solution to be titrated,
    (b) an ion source reservoir comprising an ion source solution of selected ions, positive or negative,
    (c) an ion exchange membrane barrier capable of passing ions of one charge, positive or negative, from said ion source solution to said titration reservoir, but of blocking essentially all bulk liquid flow,
    (d) a first electrode in electrical communication with said ion source reservoir, and
    (e) a second electrode in electrical communication with said titration reservoir, said first and second electrodes being inert when a current is applied between said first and second electrodes, said second electrode being in contact with said ion exchange barrier, wherein, when current is applied between said first and second electrodes, the titrant concentration generated in said titration reservoir is generated with 100% faradaic efficiency according to the formula:

$C=60I/F$, wherein

I is the current in amperes;
    F is Faraday's constant (96, 500 coulombs/eqiv.); and
    C is the concentration of titrant generated expressed in equivalents.

2. The apparatus of claim 1 further comprising a titration detection probe disposed in said titration reservoir.

3. The apparatus of claim 1 further comprising a non-flowing sample solution to be titrated in said titration reservoir.

4. The apparatus of claim 1 further comprising a stirrer in said titration reservoir.

5. An electrolytic method for titrating a liquid sample using a titration apparatus comprising a titration reservoir for a sample solution to be titrated; a substantially non-flowing ion source reservoir comprising an ion source solution of selected ions, positive or negative; an ion exchange membrane barrier capable of transporting ions of one charge, positive or negative, from said ion source solution to said titration reservoir, but of blocking essentially all bulk liquid flow; a first electrode in electrical communication with and in contact with said ion source reservoir; and a second electrode in electrical communication with said titration reservoir and in contact with said ion exchange membrane barrier; said method comprising
    (a) applying an electrical potential between said first and second electrodes to cause said selected ions to be transported from said ion source reservoir through said membrane barrier into sample solution in said titration reservoir to titrate said sample solution to an end point, said first and second electrodes being inert during application of said potential, and
    (b) detecting said titration end point; wherein, when current is applied between said first and second electrodes, the titrant concentration generated in said titration reservoir is generated with 100% faradaic efficiency according to the formula:

$C=60I/F$, wherein

I is the current in amperes;
    F is Faraday's constant (96, 500 coulombs/eqiv.); and
    C is the concentration of titrant generated expressed in equivalents.

6. The electrolytic method of claim 5 in which said detection is performed through a probe projecting into said titration reservoir.

7. The electrolytic method of claim 5 further comprising stirring said sample solution.

8. An electrolytic titrant generator for use in a titration apparatus, comprising
    (a) an ion source reservoir,
    (b) a first electrode disposed in said ion source reservoir,
    (c) an ion exchange membrane barrier having first and second sides, the first side being adjacent to said ion source reservoir and capable of transporting ions of one charge, positive or negative, but of blocking bulk liquid flow, and
    (d) a second electrode disposed in contact with the second side of the membrane barrier, said titrant generator not including a titration reservoir container for sample solution to be titrated but being configured to be immersed in sample solution in a titration reservoir container.

9. The titrant generator of claim 8 further comprising
    (e) a mounting connector configured to mount said titrant generator in a titration reservoir container for a non-flowing sample solution to be titrated.

10. The titrant generator of claim 8 in which said first electrode is inert to acid or base.

11. The titrant generator of claim 8 in which said first electrode is not silver.

12. The titrant generator of claim 8 in which said second electrode is substantially planar and has one surface proximal to the membrane barrier and a surface distal to the membrane barrier, at least 80% of said distal electrode surface being exposed to the environment or being protected by a removable cover which, when removed, is at least 80% exposed to the environment.

13. The titrant generator of claim 8 in combination with a titration reservoir, said titrant generator being mounted to said titration reservoir so that said second electrode is disposed to be immersed in sample solution in said titration reservoir.

* * * * *